(12) United States Patent
Wu et al.

(10) Patent No.: US 10,982,217 B2
(45) Date of Patent: Apr. 20, 2021

(54) HIGH-THROUGHPUT CARGO DELIVERY INTO LIVE CELLS USING PHOTOTHERMAL PLATFORMS

(71) Applicant: The Regents of the University of California, Oakland, CA (US)

(72) Inventors: Yi-Chien Wu, Taichung (TW); Ting-Hsiang S. Wu, Culver City, CA (US); Pei-Yu E. Chiou, Los Angeles, CA (US); Michael A. Teitell, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/771,478

(22) PCT Filed: Mar. 13, 2014

(86) PCT No.: PCT/US2014/026618
§ 371 (c)(1),
(2) Date: Aug. 28, 2015

(87) PCT Pub. No.: WO2014/151888
PCT Pub. Date: Sep. 25, 2014

(65) Prior Publication Data
US 2016/0017340 A1   Jan. 21, 2016

Related U.S. Application Data

(60) Provisional application No. 61/799,222, filed on Mar. 15, 2013.

(51) Int. Cl.
| | | |
|---|---|---|
| *C12N 15/64* | (2006.01) | |
| *C12N 15/87* | (2006.01) | |
| *C23C 30/00* | (2006.01) | |
| *C12M 1/42* | (2006.01) | |
| *C12N 13/00* | (2006.01) | |
| *C12N 5/071* | (2010.01) | |

(52) U.S. Cl.
CPC ............ *C12N 15/64* (2013.01); *C12M 35/02* (2013.01); *C12N 5/0602* (2013.01); *C12N 13/00* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 4,917,462 A | 4/1990 | Lewis et al. | |
| 5,080,586 A | 1/1992 | Kawai | |
| 5,310,674 A | 5/1994 | Weinreb et al. | |
| 6,052,286 A * | 4/2000 | Worthen | H01R 4/04 257/703 |
| 6,468,657 B1 * | 10/2002 | Hou | B32B 15/08 427/2.11 |
| 6,518,543 B1 | 2/2003 | Benz et al. | |
| 6,866,885 B1 | 3/2005 | Clough | |
| 7,897,377 B2 | 3/2011 | Stoppini | |
| 10,435,661 B2 | 10/2019 | Chiou et al. | |
| 10,472,651 B2 | 11/2019 | Wu et al. | |
| 2002/0023903 A1 | 2/2002 | Ann Ngoi et al. | |
| 2002/0099356 A1 | 7/2002 | Unger et al. | |
| 2003/0166181 A1 | 9/2003 | Rubinsky et al. | |
| 2003/0180946 A1 | 9/2003 | Karube et al. | |
| 2003/0235385 A1 * | 12/2003 | Taylor | G02B 6/13 385/129 |
| 2004/0079195 A1 | 4/2004 | Perry et al. | |
| 2004/0084304 A1 | 5/2004 | Thompson | |
| 2004/0084370 A1 | 5/2004 | Singh et al. | |
| 2004/0101822 A1 | 5/2004 | Wiesner et al. | |
| 2004/0158137 A1 | 8/2004 | Eppstein et al. | |
| 2006/0047254 A1 | 3/2006 | Akahoshi et al. | |
| 2006/0062902 A1 | 3/2006 | Sager et al. | |
| 2006/0110817 A1 | 5/2006 | Nishiyama et al. | |
| 2006/0115971 A1 | 6/2006 | Bau et al. | |
| 2006/0251874 A1 | 11/2006 | McClure et al. | |
| 2007/0173470 A1 | 7/2007 | Lin et al. | |
| 2008/0268540 A1 | 10/2008 | Ito et al. | |
| 2010/0040549 A1 | 2/2010 | Halas et al. | |
| 2010/0303722 A1 * | 12/2010 | Jin | A61L 27/30 424/9.1 |

(Continued)

FOREIGN PATENT DOCUMENTS

| | | |
|---|---|---|
| EP | 1 448 771 B1 | 1/2007 |
| JP | H01-141582 A | 6/1989 |

(Continued)

OTHER PUBLICATIONS

Heinemann et al, Gold Nanoparticle Mediated Laser Transfection for Efficient siRNA Mediated Gene Knock Down, PLOS ONE, 2013, pp. 1-9.*
Xia et al, Gold Nanocages: From Synthesis to Theranostic Applications, Accounts of Chemical Research, 2011, pp. 914-924.*
Yue et al, Study of transportation of atrazine and paraquat through nanochannels, Journal of Membrane Science 356 (2010) 117-122.*
Adar, F, Raman Polarization Measurements: Keeping Track of the Instrumental Components' Behavior, 2017, Spectroscopy, pp. 14-22.*
Shvedov et al, Optical guiding of absorbing nanoclusters in air, Optics Express vol. 17, Issue 7, pp. 5743-5757 (2009).*

(Continued)

*Primary Examiner* — Maria Marvich
(74) *Attorney, Agent, or Firm* — Tom Hunter; Weaver Austin Villeneuve & Sampson LLP

(57) ABSTRACT

Methods, devices, and systems are provided for the delivery of agents (e.g., nucleic acids, proteins, organic molecules, organelles, antibodies or other ligands, 5 etc.) into live cells and/or the extraction of the same from said cells. In various embodiments the photothermal platforms and systems incorporating such photothermal platforms are provided that permit efficient, high-throughput cargo delivery into live cells.

15 Claims, 11 Drawing Sheets

(56) References Cited

U.S. PATENT DOCUMENTS

| | | | |
|---|---|---|---|
| 2011/0117648 A1 | 5/2011 | Chiou et al. | |
| 2012/0160095 A1* | 6/2012 | Gin | B01D 53/22 |
| | | | 95/45 |
| 2012/0245042 A1 | 9/2012 | Liu et al. | |
| 2015/0044751 A1* | 2/2015 | Chiou | C12M 35/02 |
| | | | 435/173.6 |
| 2015/0197720 A1 | 7/2015 | Chiou et al. | |
| 2017/0175139 A1 | 6/2017 | Wu et al. | |

FOREIGN PATENT DOCUMENTS

| | | |
|---|---|---|
| JP | H08-290377 A | 11/1996 |
| JP | 2000-023657 A | 1/2000 |
| JP | 2002-536187 A | 10/2002 |
| JP | 2004-041023 A | 2/2004 |
| JP | 2005-510236 A | 4/2005 |
| JP | 2006-515758 A | 6/2006 |
| JP | 2008-237221 A | 10/2008 |
| JP | 2008-238184 A | 10/2008 |
| JP | 2011-067176 A | 4/2011 |
| WO | WO 98/20109 A1 | 5/1998 |
| WO | WO 99/46588 | 9/1999 |
| WO | WO 2003/083480 A1 | 10/2003 |
| WO | WO 2004/063350 A2 | 7/2004 |
| WO | WO 2007/008609 A2 | 1/2007 |
| WO | WO 2008/073851 A2 | 6/2008 |
| WO | WO 2008/127743 A2 | 10/2008 |
| WO | WO 2009/017695 A1 | 2/2009 |
| WO | WO 2012/158631 A2 | 11/2012 |
| WO | WO 2014/151888 A1 | 9/2014 |
| WO | WO 2015/148842 A1 | 10/2015 |

OTHER PUBLICATIONS

Bruening and Adusumilli, Polyelectrolyte Multilayer Films and Membrane Functionalization, Material Matters, 2011 vol. 6 No. 3, pp. 1-6.*
Buruiana et al, Transparent Dielectric Materials, Chapter 5, Taylor & Francis Group, 2018, pp. 96-123.*
Boudes et al. (2008) "Single-cell electroporation of adult sensory neurons for gene screening with RNA interference mechanism," *J. Neurosci. Methods*, 170:204-211.
Cao et al. (2007) "Plasmon-Assisted Local Temperature Control to Pattern Individual Semiconductor Nanowires and Carbon Nanotubes" *Nano Lett.* 7(11):3523-3527.
Chu et al. (1987) "Electroporation for the efficient transfection of mammalian cells with DNA," *Nucleic Acids Res.*, 15(3):1311-1326.
Clark et al. (2006) "Optoinjection for efficient targeted delivery of a broad range of compounds and macromolecules into diverse cell types," *J. Biomed. Opt.*, 11(1):014034(1-8).
Enders et al. (2006) "Reversible adsorption of Au nanoparticles on SiO$_2$/Si: An in situ ATR-IR study," *Surface Science*, 600(6):L71-L75, [retrieved on Nov. 7, 2008 from the Internet: http://www.sciencedirect.com/science?_ob=ArticleURL&_udi=B6TVX-4J5T4WS-7&_user=10&_rdoc=1&_fmt=&_orig=search&_sort=d&view=c&_acct=C000050221&_version=1&_urlVersion=0&_userid=10&md5=2e06d566ab4cc63face36f61c56446b5] Abstract only, 2pp.
Han et al. (2008) "High-efficiency DNA injection into a single human mesenchymal stem cell using a nanoneedle and atomic force microscopy," *J. Nanomed. Nanotechnol. Biol. Med.*, 4(3):215-225.
Hellman et al. (2008) "Biophysical Response to Pulsed Laser Microbeam-Induced Cell Lysis and Molecular Delivery," *J. Biophoton.*, 1(1):24-35.
Hirst et al. (2005) "Microchannel Systems in Titanium and Silicon for Structural and Mechanical Studies of Aligned Protein Self-Assemblies," *Langmuir*, 21(9):3910-3914.
Hurtig et al. (2008) "Injection and transport of bacteria in nanotube-vesicle networks," *Soft Matter*, 4:1515-1520.
Jain et al. (2007) "Au nanoparticles target cancer," *Nano Today*, 2(1):18-29.

Kitamura et al. (2008) "Targeted patch-clamp recordings and single-cell electroporation of unlabeled neurons in vivo," *Nat. Methods*, 5(1):61-67.
Kotaidis et al. (2006) "Excitation of nanoscale vapor bubbles at the surface of gold nanoparticles in water," *The Journal of Chemical Physics*, 124:184702(1-7).
Laffafian et al. (1998) "Lipid-assisted microinjection: introducing material into the cytosol and membranes of small cells," *Biophys. J.*, 75:2558-2563.
Lapotko et al. (2006) "Selective laser nano-thermolysis of human leukemia cells with microbubbles generated around clusters of gold nanoparticles," *Laser Surg. Med.*, 38:631-642.
Lee et al. (2009) "Remote Optical Switch for Localized and Selective Control of Gene Interference," *Nano Lett.*, 9(2):562-570.
Lin et al. (Jun. 21-25, 2015) "Shape Anisotropic Magnetic Particles for High Throughput and High Efficiecy Intracelluar Delivery of Functional Macromolecules," *IEEE, Transducers 2015, 18th International Conference on Solid-State Sensors, Actuators and Microsystems (Transducers)*, Anchorage, Alaska, USA, pp. 880-883.
Link et al (1999) "Spectral Properties and Relaxation Dynamics of Surface Plasmon Electronic Oscillations in Gold and Silver Nanodots and Nanorods," *J. Phys. Chem. B*, 103(40):8410-8426.
Liu et al. (2005) "Optofluidic control using photothermal nanoparticles," *Nat. Mater.*, 5:27-32.
Lokhandwalla et al. (2001) "Mechanical haemolysis in shock wave lithotripsy (SWL): I. Analysis of cell deformation due to SWL flow-fields," *Phys. Med. Biol.*, 46:413-437.
Lukianova-Hleb et al. (2010) "Plasmonic Nanobubbles as Transient Vapor Nanobubbles Generated around Plasmonic Nanoparticles," *ACS Nano*, 4(4):2109-2123.
Marmottant et al. (2003) "Controlled vesicle deformation and lysis by single oscillating bubbles," *Nature*, 423:153-156.
Mitragotri (2005) "Innovation—Healing sound: the use of ultrasound in drug delivery and other therapeutic applications," *Nat. Rev. Drug Discovery*, 4(3):255-260.
Parker et al. (Jul. 13, 2010) "Bulk Titanium Microfluidic Networks for Protein Self-Assembly Studies," [Retrieved on Oct. 23, 2014 from the Internet at URL:http://www.engineering.ucsb.edu/memsucsb/Research/publications/parker_microtas05.pdf], 4 pages.
Pitsillides et al. (2003) "Selective cell targeting with light-absorbing microparticles and nanoparticles," *Biophys. J.*, 84(6):4023-4032.
Prodan et al. (2003) "A Hybridization Model for the Plasmon Response of Complex Nanostructures," *Science*, 302:419-422.
Qiu et al. (2009) "Microchip CE analysis of amino acids on a titanium dioxide nanoparticles-coated PDMS microfluidic device with in-channel indirect amperometric detection," *Electrophoresis*, 30(19):3472-3479.
Skirtach et al. (2005) "The Role of Metal Nanoparticles in Remote Release of Encapsulated Materials," *Nano Lett.*, 5(7):1371-1377.
Stevenson et al. (2006) "Femtosecond optical transfection of cells:viability and efficiency," *Opt. Express*, 14(16):7125-7133.
Suzuki et al. (2010) "A Cell Array Fabricated by Assembly-Free Multidirectional Photolithography," *Journal of Japan Institute of Electronics Packaging*, 13(3):194-199.
Tirlapur et al. (2002) "Cell biology: Targeted transfection by femtosecond laser," *Nature*, 418:290-291.
Vogel et al. (2005) "Mechanisms of femtosecond laser nanosurgery of cells and tissues," *Appl. Phys. B: Laser Opt.*, 81(8):1015-1047.
Waje et al. (2005) "Deposition of platinum nanoparticles on organic functionalized carbon nanotubes grown in situ on carbon paper for fuel cells," *Nanotechnology*, 16:S395-S400.
Wu et al. (Jul. 21, 2008) "Light Image Patterned Molecular Delivery into Live Cells Using Gold Particle Coated Substrate," *IEEE/LEOS Summer Topical Meetings, 2008 Digest of the IEEE*, Piscataway, NJ, USA, pp. 195-196.
Wu et al. (Feb. 7, 2010) "Molecular Delivery Into Live Cells Using Gold Nanoparticle Arrays Fabricated by Polymer Mold Guided Near-Field Photothermal Annealing," *Proceedings of ASME 2010 First Global Congress on NanoEngineering for Medicine and Biology*, Houston Texas, USA, pp. 121-122.
Wu et al. (2010) "Image patterned molecular delivery into live cells using gold particle coated substrates," *Opt. Express*, 18(2):938-946.

(56) References Cited

OTHER PUBLICATIONS

Wu et al. (2010) "Photothermal nanoblade for patterned cell membrane cutting," *Optics Express*, 18(22):23153-23160.
Wu et al. (2011) "Photothermal nanoblade for Large Cargo Delivery into Mammalian Cells," *Anal. Chem.*, 83(4):1321-1327.
Wu et al. (May 1, 2015) "Massively parallel delivery of large cargo into mammalian cells with light pulses," *HHS Public Access Author Manuscript*, 12(5):439-444 and Supplementary information (Apr. 6, 2015) 2pp.
Zhang, Y. (2007) "Microinjection technique and protocol to single cells," *Nat. Protoc.* published online Nov. 2, 2007 [retrieved on May 13, 2011 at 3:04 PM from the Internet at http://www.natureprotocols.com/2007/11/02/microinjection_technique_and_p.php], pp. 1-11.
Zhao et al. (2009) "Wafer level bulk titanium ICP etching using SU8 as an etching mask," *J. Micromech. Microeng.*, 19(9):95006, 10pp.
Menon and Martin (1995) "Fabrication and Evaluation of Nanoelectrode Ensembles," *Anal. Chem.*, 67(13): 1920-1928.
European Extended Search Report dated Feb. 9, 2018 issued in EP 15769138.7.
Adar (2017) "Raman Polarization Measurements: Keeping Track of the Instrumental Components" *Spectroscopy*, 32(2): 14-22.
Shi et al. (2010) "Pressure Regulated Biomolecule Injection Into NIH 3T3 Cells Through Integrated Nano/Mesopores", *14th International Conference on Miniaturized Systems for Chemistry and Life Sciences Oct. 3-7, 2010*, Groningen, The Netherlands, pp. 491-493, Retrieved from the Internet: URL:http://www.rsc.orgjbinariesjlocj2010/pdfs/Papers/171 0548.pdf [retrieved on Oct. 24, 2017].
Madeira, et al. (2010) "Nonviral Gene Delivery to Mesenchymal Stem Cells Using Cationic Liposomes for Gene and Cell Therapy," *Journal of Biomedicine and Biotechnology*, vol. 2010, Article ID 73539, pp. 1-12.
U.S. Notice of Allowance dated May 7, 2019 issued in U.S. Appl. No. 14/523,254.
U.S. Office Action dated Mar. 22, 2019 issued in U.S. Appl. No. 15/129,387.
U.S. Notice of Allowance dated Jul. 31, 2019 issued in U.S. Appl. No. 15/129,387.
Canadian Office Action dated Mar. 14, 2019 issued in CA 2,873,204.
Shi et al. (2004) "Myogenic fusion of human bone marrow stromal cells, but not hematopoietic cells", *Blood* 104(1): 290-294.
Yu et al. (2012) "Gold Coated Block Copolymer Membranes with Precisely Controllable Pore Size for Molecule Separations," *Procedia Engineering*, 44: 1639-1641.

\* cited by examiner

HIGH-THROUGHPUT CARGO DELIVERY INTO LIVE CELLS USING PHOTOTHERMAL PLATFORMS

CROSS-REFERENCE TO RELATED APPLICATIONS

This application is a U.S. 371 National Phase of PCT/US2014/026618, filed Mar. 13, 2014, which claims benefit of and priority to U.S. Ser. No. 61/799,222, filed on Mar. 15, 2013, each of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. EB014456, awarded by the National Institutes of Health. The Government has certain rights in the invention.

BACKGROUND

Transferring cargo into mammalian cells over a wide range of sizes, including proteins, DNA, RNA, chromosomes, nuclei, and inanimate particles, such as quantum dots, surface-enhanced Raman scattering (SERS) particles, and microbeads, is highly desirable in many fields of biology. Delivery methods, such as endocytosis, can entrap cargo in an endosome, where the low pH microenvironment and lytic enzymes often lead to cargo degradation (Luo and Saltzman (2000) Nat. Biotechnol. 18: 33-37). Viral and chemical delivery methods package the cargo inside a virus or form chemical complexes that enhance uptake (Naldini et al. (1996) Science, 272: 263-267; Feigner et al. (1987) Proc. Natl. Acad. Sci. USA, 84: 7413-7417). However, toxicity, cell-type specific uptake, and more importantly limited cargo packing capacity impose a significant constraint on cargo size and transferable cell types (Luo and Saltzman, supra.).

Physical transfer methods include electroporation (Chu, et al. (1987) Nucleic Acids Res. 15: 1311-1326) and sonoporation (Mitragotri (2005) Nat. Rev. Drug Discovery, 4: 255-260), which are methods that produce randomly distributed nanoscale pores, and optoporation (Tirlapur and Konig (2002) Nature, 418: 290-291; Vogel, et al. (2005) Appl. Phys. B: Laser Opt., 81: 1015-1047; Clark et al. (2006) J. Biomed. Opt., 11: 014034), which is a method that generates pores on the cell membrane at the laser focal point. Small cargos are delivered through these pores into cells by thermal diffusion or by an electric field. Delivery of large cargo with these methods, however, has low efficiency due to the slow speed of cargo diffusion and decreasing cell viability with increasing pore size (Stevenson et al. (2006) Opt. Express, 14: 7125-7133).

Microcapillary injection uses a sharp glass tip to mechanically penetrate a cell membrane for delivery (see, e.g., King (2004) Meth. Mo. Biol., 245: Gene Delivery to Mammalian Cells 1; Humana Press Inc. Totowa, N.J.). However, mechanical trauma from membrane penetration limits the typical pipet tip to about 0.5 um in diameter in order to maintain cell viability (see, e.g., Han et al. (2998) J. Nanomed. Nanotechnol. Biol. Med., 4: 215-225).

Cargos larger than the pipet tip cannot be injected due to pipet clogging and cargo shearing. Electro-injection, a method that combines electroporation with microcapillary injection, has demonstrated delivery of small molecules such as RNA and plasmid DNA, into live cells (see, e.g., Boudes et al. (208) J. Neurosci. Meth., 170: 204-211; Kitamura et al. (2008) Nat. Meth., 5: 61-67, and the like) and bacteria delivery into artificial lipid vesicles (see, e.g., Hurtig and Orwar (2008) Soft Matter, 4: 1515-1520). Electro-injection works by weakening the cell membrane with an electric field, followed by gentle mechanical penetration into the cell.

Simple lipid assisted microinjection (SLAM) techniques (Laffafian and Hallett (1998) Biophys. J., 75: 2558-2563) incorporate synthetic lipid molecules at the tip of a glass microcapillary. Contact of the SLAM micropipette with a cell membrane allows the lipid molecules to fuse with the cell membrane to form a continuous and temporary pathway for cargo delivery. This method avoids problematic zigzag stabbing motions of the micropipette tip through the cell membrane. However, the lipohilic interactions with cargo and cell membrane can produce unwanted biological effects in the cell as well as with the delivery cargo, limiting this method to specific cell types and cargo contents.

SUMMARY

In certain embodiments, methods, devices, and systems are provided for the delivery of agents (e.g., nucleic acids, proteins, organic molecules, organelles, antibodies or other ligands, etc.) into live cells and/or the extraction of the same from said cells. In various embodiments photothermal platforms and systems incorporating such photothermal platforms are provided that permit efficient, high-throughput cargo delivery into live cells.

In various aspects, the invention(s) contemplated herein may include, but need not be limited to, any one or more of the following embodiments:

Embodiment 1

A device for delivering an agent into a cell, said device including a porous membrane having deposited thereon a thin film coating a material that heats up when exposed to optical radiation, wherein said thin film coating is deposited substantially within pores including said porous membrane and the surface of said porous membrane is substantially free of said coating.

Embodiment 2

The device of embodiment 1, wherein the average pore size of said porous membrane ranges from about 100 nm up to about 3 µm before deposition of said thin film.

Embodiment 3

The device according to any one of embodiments 1-2, wherein said thin film includes a material selected from the group consisting of gold, silver, titanium (Ti), TiN, TiCn, and TiAlN.

Embodiment 4

The device according to any one of embodiments 1-2, wherein said thin film includes titanium.

Embodiment 5

The device according to any one of embodiments 1-4, wherein said thin film ranges in thickness from about 10 nm up to about 1 µm.

Embodiment 6

The device according to any one of embodiments 1-5, wherein said porous membrane includes a porous alumina ($Al_2O_3$) structure.

Embodiment 7

The device according to any one of embodiments 1-5, wherein said porous membrane includes a polyester membrane.

Embodiment 8

The device according to any one of embodiments 1-7, wherein said porous membrane is contacted to or juxtaposed adjacent to a plurality of cells.

Embodiment 9

The device of embodiment 8, wherein said cells are mammalian cells.

Embodiment 10

A device for delivering an agent into a cell, said device including: a rigid substrate including a first surface and a second surface on the side opposite said first surface and an array of micro-orifices, where said micro-orifices that penetrate through said substrate from said first surface to said second surface, where said micro-orifices have a maximum diameter of less than about 10 μm and at least a portion of a wall or lip of a plurality of said micro-orifices and/or regions of said first surface adjacent to said micro-orifices is coated with a thin film coating of a material that heats up when exposed to optical radiation; and a fluid channel or fluid reservoir disposed adjacent to said second surface where said channel or reservoir is in fluid communication with a plurality of micro-orifices including said array of micro-orifices; and where the face of said first surface is disposed to receive and support and/or contain cells.

Embodiment 11

The device of embodiment 10, wherein said micro-orifices have a maximum diameter about 5 μm or less.

Embodiment 12

The device of embodiment 10, wherein said micro-orifices have a maximum diameter about 3 μm or less.

Embodiment 13

The device according to any one of embodiments 10-12, wherein said rigid substrate is formed from a microlithographic wafer.

Embodiment 14

The device according to any one of embodiments 10-13, wherein said rigid substrate is formed from a material selected from the group consisting of silicon, quartz, a rigid polymer, and a ceramic.

Embodiment 15

The device according to any one of embodiments 10-13, wherein said rigid substrate is formed from silicon.

Embodiment 16

The device according to any one of embodiments 10-15, wherein said rigid substrate, wherein said first surface includes a surface of a chamber configured to contain cells and disposed for viewing with a microscope.

Embodiment 17

The device of embodiment 16, wherein said chamber has an open top.

Embodiment 18

The device of embodiment 16, wherein said chamber has a top closing the chamber.

Embodiment 19

The device according to any one of embodiments 10-18, wherein said array of micro-orifices includes at least 5, at least 10, at least 15, at least 20, at least 25, at least 50, at least 100, at least 200, or at least 500 micro-orifices.

Embodiment 20

The device of embodiment 19, wherein said orifices are all located within an area of said surface of about 2 $cm^2$ or less, or within about 1.5 $cm^2$ or less, or within about 1 $cm^2$ or less, or within about 0.5 $cm^2$ or less, or within about 0.1 $cm^2$ or less.

Embodiment 21

The device according to any one of embodiments 10-20, wherein said thin film is deposited on a portion of a wall and/or a portion of the lip of the micro-orifice(s).

Embodiment 22

The device according to any one of embodiments 10-21, wherein said thin film includes a material selected from the group consisting of a semiconductor, a metal, a metal alloy, a metal nitride, and a metal oxide.

Embodiment 23

The device of embodiment 22, wherein said thin film includes a material selected from the group consisting of a transition metal, a transition metal alloy, a transition metal nitride, and a transition metal oxide.

Embodiment 24

The device of embodiment 22, wherein said thin film includes a material selected from the group consisting of gold, silver, titanium (Ti), TiN, TiCn, and TiAlN.

Embodiment 25

The device according to any one of embodiments 10-24, wherein said fluid channel or chamber device contains a reagent to be delivered into a cell.

Embodiment 26

The device of embodiments 25, wherein said reagent is selected from the group consisting of a nucleic acids, a ribozyme, a protein or peptide, an enzyme, an antibody, an organelle, a chromosome, a pathogen, and a microparticle or nanoparticle.

Embodiment 27

The device according to any one of embodiments 10-26, wherein said channel or chamber is pressurized.

Embodiment 28

The device of embodiment 27, wherein said channel or chamber is pressurized by gas pressure, a pump, or a gravity feed.

Embodiment 29

The device according to any one of embodiments 10-28, wherein said device is configured to replace the stage on an inverted microscope.

Embodiment 30

The device according to any one of embodiments 10-29, wherein a cell is disposed on said first surface.

Embodiment 31

The device of embodiment 30, wherein said cell is disposed on or adjacent to a plurality of micro-orifices in said substrate.

Embodiment 32

The device according to any one of embodiments 30-31, wherein said cell is a mammalian cell.

Embodiment 33

A system for selectively opening delivering an agent into a cell, said system including: a device according to any one of embodiments 1-9; and/or a device according to any one of embodiments 10-32; and a source of optical energy capable of heating said thin film.

Embodiment 34

The system of embodiment 33, wherein said source of optical energy is a laser or a non-coherent light source.

Embodiment 35

The system of embodiment 34, wherein said source of optical energy is a laser.

Embodiment 36

The system according to any one of embodiments 33-35 of embodiment wherein said system includes a lens system, a mirror system, and/or a mask, and/or a positioning system to directing the optical energy to a specific region of said first surface or said porous membrane.

Embodiment 37

The system according to any one of embodiments 33-36, wherein said system includes an objective lens configured to focus optical energy onto said first surface or said porous membrane.

Embodiment 38

The system of embodiment 37, wherein said system includes a half-wave plate.

Embodiment 39

The system according to any one of embodiments 37-38, wherein said system includes a polarizer.

Embodiment 40

The system of embodiment 39, wherein said polarizer includes a polarizing beam splitter cube.

Embodiment 41

The system according to any one of embodiments 33-40, wherein said system includes a controller that adjusts at least one of the pattern of illumination by said optical energy source, the timing of occurrence of light pulses emitted by the optical energy source, the frequency of occurrence of pulses emitted by the optical energy source, the wavelength of pulses emitted by the optical energy source, the energy of pulses emitted by the optical energy source, and the aiming or location of pulses emitted by the optical energy source.

Embodiment 42

A method of delivering a reagent into a cell, said method including: providing cells in device according to any one of embodiments 1-9, or 10-29 and/or in a system according to any one of embodiments 33-41, wherein said cells are disposed on said first surface or contacted to or juxtaposed near said porous membrane; contacting said cells with said reagent; and exposing a region of said surface or porous membrane to optical radiation thereby inducing heating of said thin film where said heating forms bubbles that introduce openings in the membrane of cells in or near the heated region resulting in the delivery of said reagent into those cells.

Embodiment 43

The method of embodiment 42, wherein said method includes providing cells on a device according to any one of embodiments 1-9, or in a system according to any one of embodiments 33-41 incorporating said porous membrane.

Embodiment 44

The method according to any one of embodiments 42-43, wherein said cells are contacted with said reagent by providing said reagent in culture medium surrounding the cells.

Embodiment 45

The method according to any one of embodiments 42-44, wherein cells are placed or grown on the top of said porous membrane and the surface of said membrane at or near said cells is heated.

Embodiment 46

The method according to any one of embodiments 42-44, wherein cells are placed or grown on the top of said porous membrane and the surface of said membrane opposite said cells is heated.

Embodiment 47

The method according to any one of embodiments 42-44, wherein cells are placed or grown on a separate substrate and said porous membrane is positioned on top of said cell(s) for reagent delivery.

Embodiment 48

The method of embodiment 47, wherein said separate substrate includes a surface of an object selected form the group consisting of a coverslip, a microtiter plate, a petri dish, and a culture vessel.

Embodiment 49

The method of embodiment 42, wherein said method includes providing cells on a device according to any one of embodiments 10-29, or in a system according to any one of embodiments 33-41 incorporating said rigid substrate.

Embodiment 50

The method according to any one of embodiments 42 or 49, wherein said cells are contacted with said reagent by providing said reagent in one or more orifices that are present in said surface.

Embodiment 51

The method of embodiment 50, wherein said cells are contacted with said reagent by providing said reagent in chamber or channel in fluid communication with said micro-orifices.

Embodiment 52

The method according to any one of embodiments 32-51, wherein said exposing includes exposing a region of said surface to a laser pulse or to a non-coherent light source.

Embodiment 53

The method according to any one of embodiments 32-52, wherein said reagent is selected from the group consisting of a nucleic acid, a chromosome, a protein, a label, an organelle, and a small organic molecule.

Embodiment 54

A method of delivering a reagent into a cell, said method including: providing cells on a substrate substantially lacking nanoparticles or a thin film; contacting said cells with said reagent; and exposing a region of said substrate to optical radiation thereby inducing heating of substrate where said heating forms bubbles that introduce openings in the membrane of cells in or near the heated region resulting in the delivery of said reagent into those cells.

Embodiment 55

The method of embodiment 54, wherein said substrate is formed from a material selected from the group consisting of silicon, quartz, a rigid polymer, a metal, and a ceramic.

Embodiment 56

The method of embodiment 54, wherein said substrate is formed from silicon.

Embodiment 57

The method according to any one of embodiments 54-56, wherein said substrate includes a surface of a chamber configured to contain cells.

Embodiment 58

The method of embodiment 57, wherein said substrate is disposed for viewing with a microscope.

Embodiment 59

The method according to any one of embodiments 57-58, wherein said chamber has an open top.

Embodiment 60

The method according to any one of embodiments 57-58, wherein said chamber has a top closing the chamber.

Embodiment 61

The method according to any one of embodiments 54-60, wherein said reagent is selected from the group consisting of a nucleic acids, a ribozyme, a protein or peptide, an enzyme, an antibody, an organelle, a chromosome, a pathogen, and a microparticle or nanoparticle.

Embodiment 62

The method according to any one of embodiments 54-61, wherein said substrate is configured to be place on or to replace the stage on an inverted microscope.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose a carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The term "reagent(s)" when used with respect to substances to be delivered into cells include any substance that is to be delivered into (or extracted from) a cell. Such reagents include, but are not limited to nucleic acids (including, for example, vectors and/or expression cassettes, inhibitory RNAs (e.g., siRHA, shRNA, miRNA, etc.), ribozymes, proteins/peptides, enzymes, antibodies, imaging reagents, organelles (e.g., nuclei, mitochondria, nucleolus, lysosome, ribosome, etc.), chromosomes, intracellular pathogens, inanimate particles, such as quantum dots, surface-enhanced, Raman scattering (SERS) particles, microbeads, and the like.

BRIEF DESCRIPTION OF THE DRAWINGS

FIG. 3A: A silicon-based photothermal delivery platform with 3 μm orifices and 50 μm channels. FIG. 3B: A deformable membrane pump made of PDMS was integrated with the silicon-based photothermal platform for active fluid pumping and cargo delivery.

FIG. 6A: A parallel delivery platform was realized by depositing a titanium thin film onto track-etched polyester porous membranes. Using pulsed laser ablation at an oblique angle, the titanium thin film at the membrane surface was removed, leaving the titanium inside the pores intact. The sidewall titanium serves as bubble induction sites after pulsed laser excitation in order to create cutting in the adjacent cell membrane. FIG. 6B: Cavitation bubbles generated on the porous membranes with average pore diameters of 3 μm and 1 μm respectively.

FIG. 8, panel B: Fluorescent dextran molecules were delivered into human embryonic stem cell (hESC) colonies cultured on matrigel coated porous membranes with high efficiency.

DETAILED DESCRIPTION

In certain embodiments, methods, devices, and systems are provided for the delivery of agents (e.g., nucleic acids, proteins, organic molecules, organelles, antibodies or other ligands, etc.) into live cells and/or the extraction of the same from said cells. In various embodiments photothermal platforms and systems incorporating such photothermal platforms are provided that permit efficient, high-throughput cargo delivery into live cells.

In various embodiments, photothermal platforms described herein utilize an optical energy source to heat a fluid and/or a surface (or a component or area thereof) and thereby form a rapidly expanding "cavitation" bubble. Without being bound by a particular theory, in various embodiments the methods, platforms, and systems described herein rely on the hydrodynamic and/or mechanical forces exerted by the bubble cavitation to locally and transiently open the cell membrane for delivery. It was discovered that this physical mechanism can be applied to a wide range of cell types and cargo (reagent) types.

Additionally, the ultrafast cell membrane cutting provided by the bubble expansion opens a micron-sized portal in the cell membrane for super-sized cargo delivery such as microbeads or organelles while maintaining cell viability.

In certain embodiments using microfabrication techniques, greater than about $10^6$ photothermal delivery sites can be realized over an area of 1 cm×1 cm in the photothermal platforms. Simultaneous delivery to greater than about $10^6$ cells can be done within few seconds by illuminating a single optical energy (e.g., laser) pulse over the effective area followed by cargo diffusion or pumping.

I. Microfabricated Surface-Based Photothermal Delivery Platform.

Figure 1A:
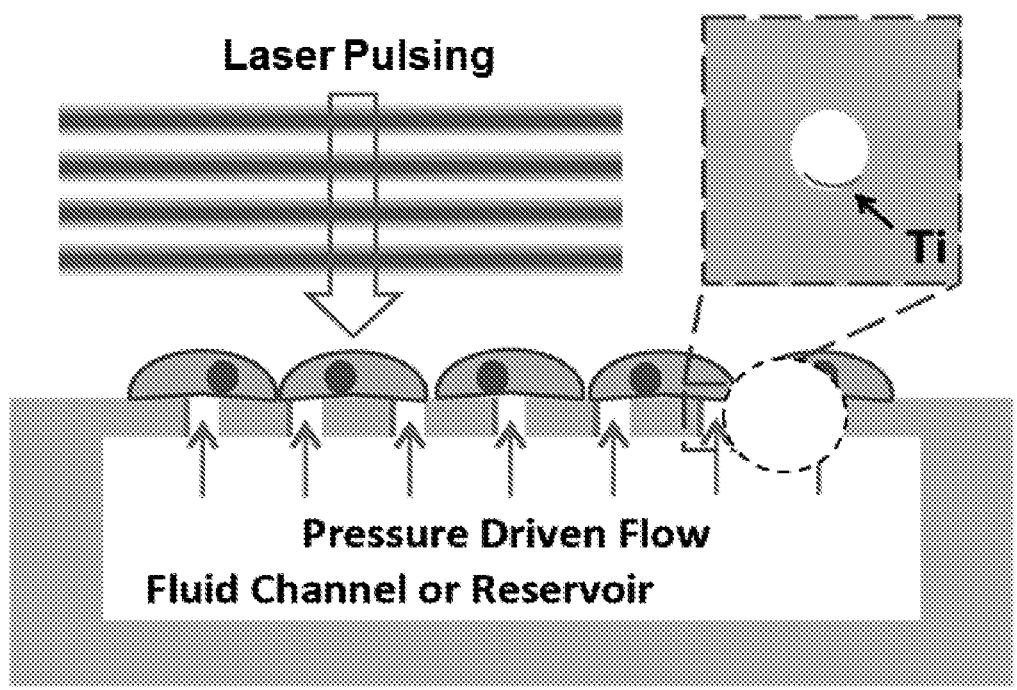
FIGS. 1A and 1B schematically illustrate one embodiment of a microfabricated photothermal platform for high-throughput cargo delivery into live mammalian cells.
Figure 1B:
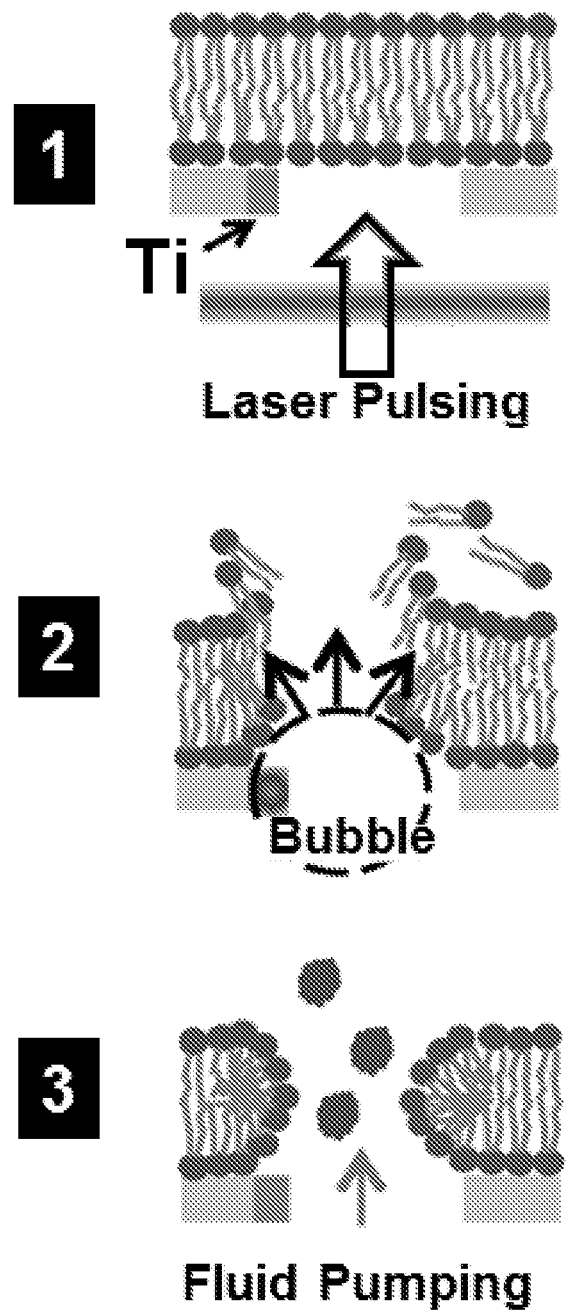

In certain embodiments a microfabricated (e.g., etched and/or deposited) surface based photothermal delivery platform is provided. FIG. 1 illustrates the principle of a silicon-based, microfabricated photothermal platform for high-throughput cargo delivery into live mammalian cells.

As illustrated in this figure, a 2D array of micro orifices with well-defined size and spacing are fabricated. Typically the micro-orifices range in size from about 100 nm up to about 4 µm. In certain embodiments the micro-orifices range in size from about 100 nm or from about 300 nm, or from about 500 nm, or from 800 nm up to about 1 µm, or up to about 2 µm, or up to about 3 µm, or up to about 4 µm, or up to about 5 µm. In various embodiments typical spacing between the micro-orifices ranges from about 1 µm to about 10 µm. The thin film can comprise any material that can be rapidly heated by optical energy source. Illustrative, but non-limiting materials include a metal, a semiconductor, and the like. In certain embodiments the material comprises gold, silver, titanium (Ti), TiN, TiCn, and TiAlN. Other metals, metal alloys, metal oxides, metal nitrides, and the like can also be used.

A thin film of formed from a material that heats up when exposed to high intensity optical energy is deposited onto the inner side and/or lip of the micro orifices. In various embodiments the thin film ranges in thickness from about 10 nm to 1 µm.

Upon pulsing with an optical energy source (e.g., a laser), the thin film (e.g., a titanium thin film) heats up and induces a crescent-shaped vapor bubble. The cavitation bubble cuts the adjacent cell membrane and creates a transient portal for cargo delivery into the cell cytosol. Various sized cargo can be transported into the cell by diffusion or active fluid pumping in synchronization with the laser pulsing.

In various embodiments the material comprising the photothermal substrate can be fabricated from any convenient material that is preferably not toxic to the cell(s), that can carry the thin film coating, and that can tolerate the local heating produced by application of electromagnetic energy (e.g., optical energy) to the surface and/or thin film. Suitable materials include, but are not limited to glass/silicon, germanium, a mineral (e.g., quartz), a ceramic, a plastic (e.g., DELRIN®, TEFLON®, etc.), a metal, a semiconductor, and the like.

In certain embodiments, the substrate comprises a surface of a vessel used for cell screening and/or for cell culture. This can include, for example, vessels for adherent or suspended cell culture. This can also include, microtiter plates (e.g., 96, 384, 864, 1536 well, etc.), microfluidic devices, high density (microarray) substrates, microscope slides or chambers, and the like.

Figure 2:
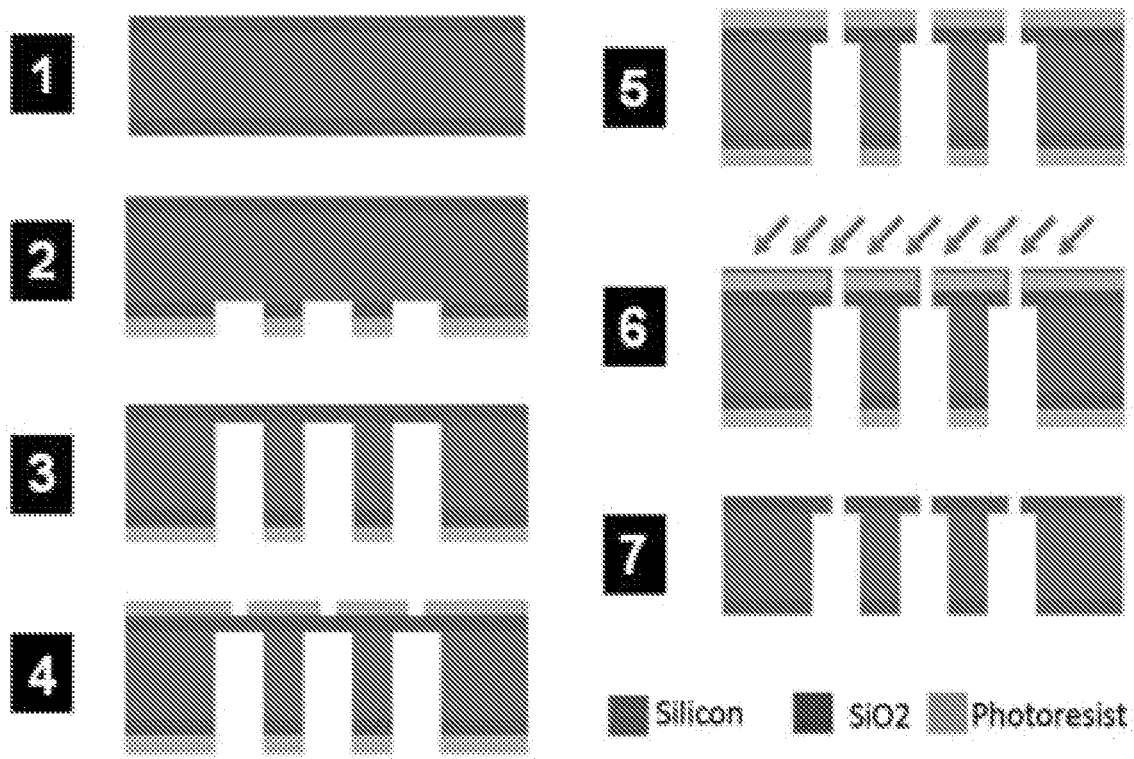
FIG. 2 illustrates one embodiment of a process flow for fabrication of silicon-based photothermal platform.

In certain embodiments the cell transfection substrates are fabricated using techniques known in the semiconductor industry. FIG. 2, schematically illustrates one process flow for fabricating a silicon-based photothermal delivery platform. SiO$_2$ thin films were deposited onto the top and bottom side of a silicon wafer. Using photolithography and dry etching, arrays of 3 micron holes were defined in the top oxide layer and large openings of 50 to 100 microns were defined in the bottom oxide layer. Titanium thin film was deposited onto the top oxide layer. Using deep reactive ion etching, silicon channels were etched from the backside through the entire thickness of the wafer until the 3 micron holes in the top oxide layer were connected followed by lift-off process to reveal the sidewall titanium coating.

While the illustrated orifices are circular, they need not be so limited. Using standard methods (e.g., etching methods) orifices of essentially any shape (e.g., round, square, pentagonal, hexagonal, ellipsoid, trapezoidal, irregular, etc.) can be produced. Similarly, the patterning of the orifices can be in essentially any desired pattern.

Figure 3A:
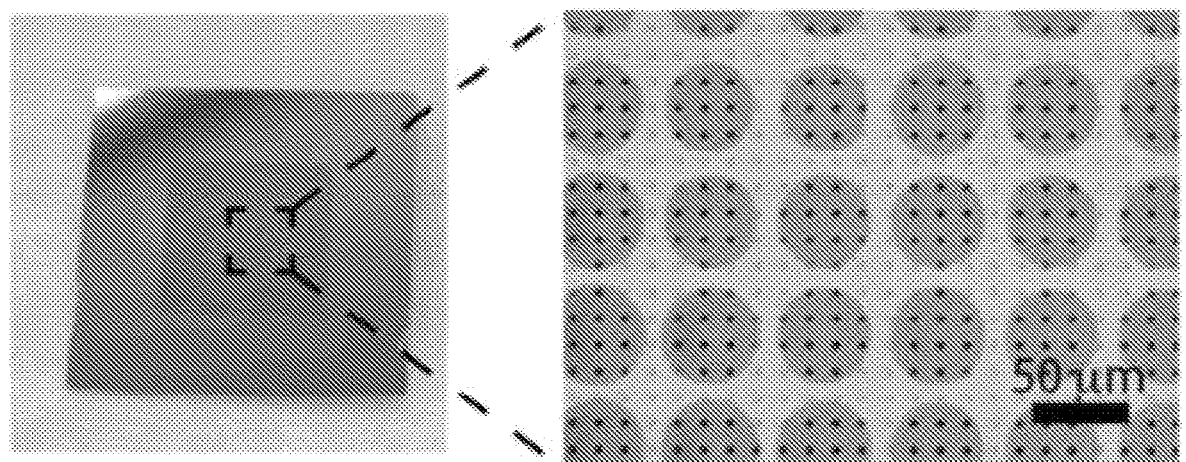
FIGS. 3A and 3B illustrate a photothermal delivery platform.
Figure 3B:
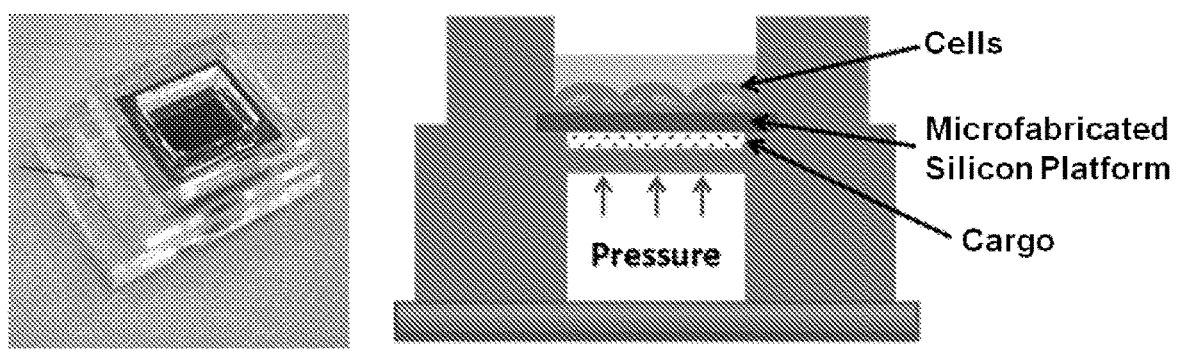

FIGS. 3A and 3B show one illustrative silicon-based photothermal delivery platform with 3 µm orifices and 50 µm channels. In order to achieve efficient delivery of large cargos, a deformable membrane pump, in this case made of PDMS was integrated with the silicon-based photothermal platform for active fluid pumping and cargo delivery. It will be recognized that other elastomeric materials (e.g., various plastics and/or other materials used for soft lithography) can be used to fabricate the membrane pump.

Figure 4:
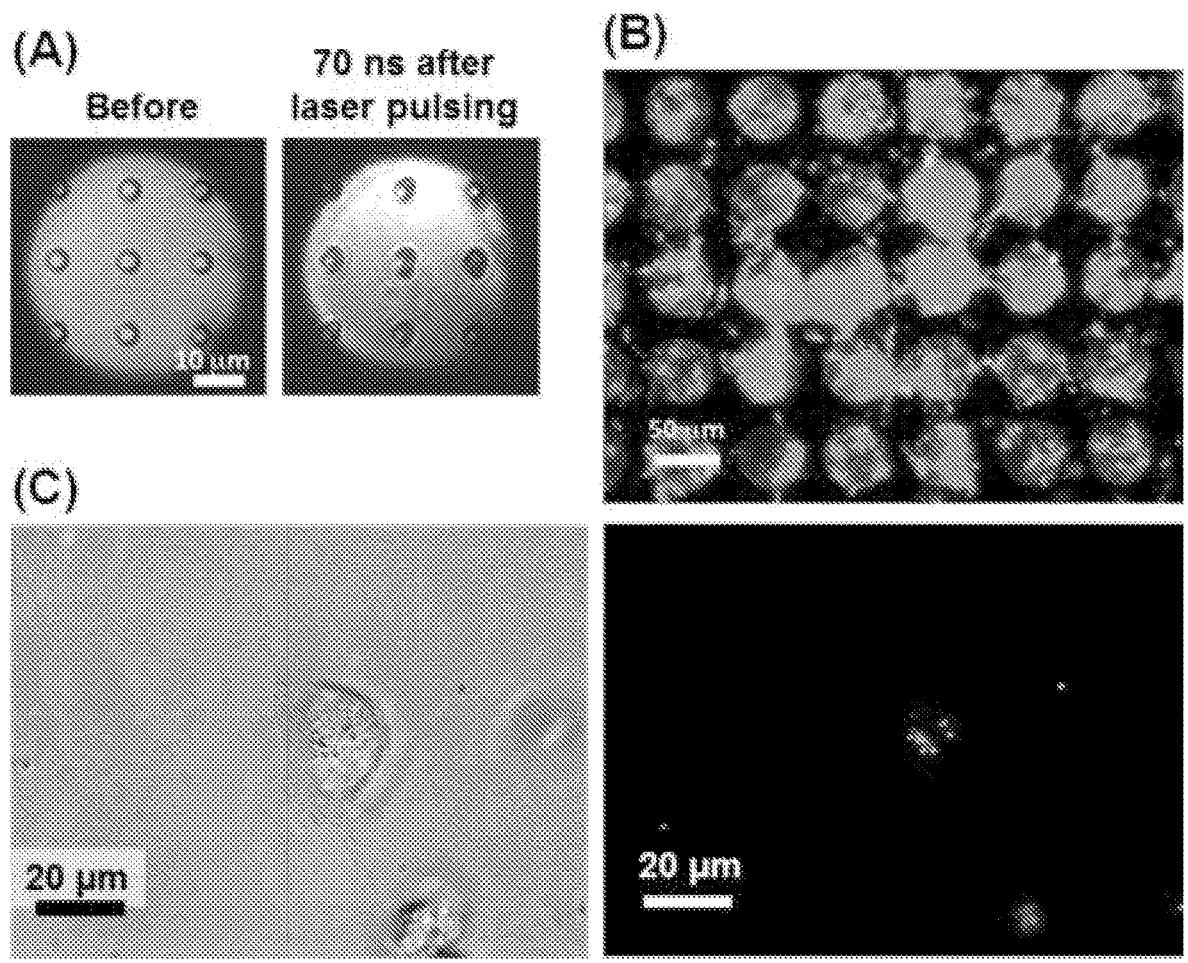
FIG. 4, panels A-C, illustrates bubble generation an reagent delivery. Panel A: Crescent shaped bubble generation on the silicon-based photothermal platform. Panel B: Delivery of 1 μm green fluorescent microbeads into HeLa cells cultured on the platform. Panel C: Bright field and fluorescent images of cells containing multiple 1 μm green fluorescent beads. The cells were re-plated onto a cell culture dish after delivery for easier observation.

FIG. 4A shows the generation of a crescent-shaped bubble after laser pulsing on the titanium thin film for cell membrane cutting. The titanium coating is robust for greater than 50 operations. Using this delivery platform, cargos as large as 1 µm polystyrene microspheres can be delivered into cells at high efficiency. FIGS. 4B and 4C show high-throughput delivery of 1 µm green fluorescent microbeads into HeLa cells over an area of 1 cm×1 cm on this platform.

Figure 5A:
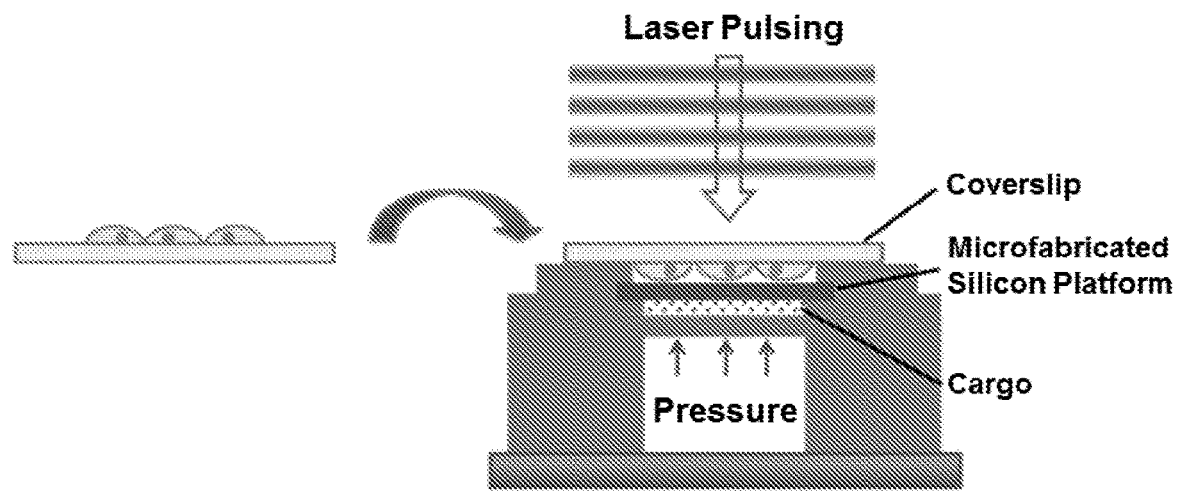
FIG. 5A illustrates one alternative configuration of for parallel cargo delivery using the microfabricated photothermal platform by inverting the cells onto the chip. Cells can be grown on a coverslip (or other transparent, planar substrates). A spacer is used between the coverslip and the silicon chip to maintain appropriate contact of the cell membrane with the titanium-coated orifices. After laser pulsing and cell membrane cutting by bubble cavitation, cargo can be driven into the cell using the deformable PDMS membrane pump.
Figure 5B:
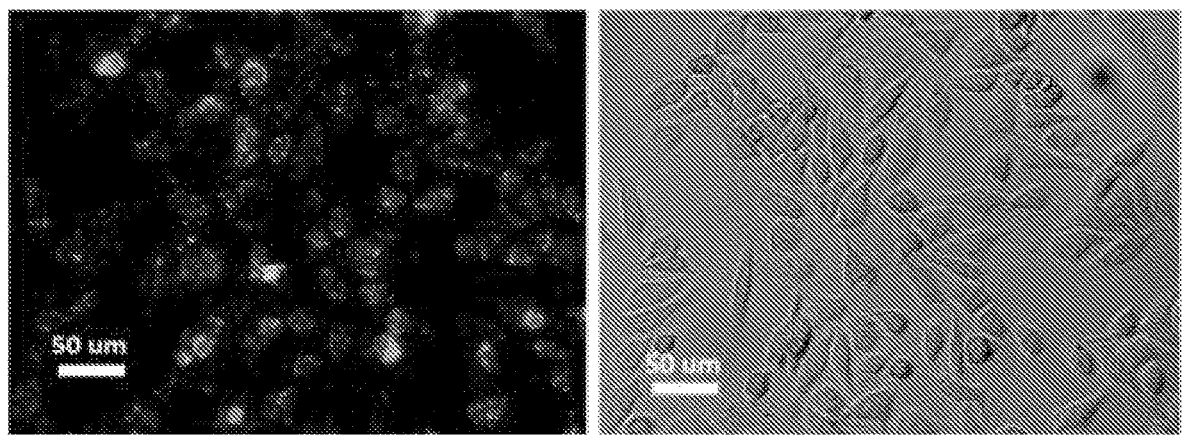
FIG. 5B shows HeLa cells cultured on a glass coverslip with delivered 200 nm fluorescent microbeads using this configuration.

One illustrative alternative configuration of parallel delivery using the silicon-based photothermal platform by inverting the cells onto the chip is illustrated in FIG. 5A. Cells can be grown on a coverslip (or other transparent, preferably planar substrates). A spacer is used between the coverslip and the silicon chip to maintain appropriate contact of the cell membrane with the titanium-coated orifices. After laser pulsing and cell membrane cutting by bubble cavitation, cargo can be driven into the cell using the deformable PDMS membrane pump (or other pumping system). FIG. 5B shows HeLa cells cultured on a glass coverslip with delivered 200 nm fluorescent microbeads using this configuration.

In certain embodiments for super-sized cargo delivery such as micron-sized particles, organelles or even bacteria, the microfabricated photothermal platform can achieve high delivery efficiency and high cell viability. In one illustrative, but non-limiting embodiment, cells are cultured on the chip. Before delivery, cargo is loaded from the back side of the chip filling the silicon channels. The PDMS pump is actuated to drive the cargo and fluid into the cell immediately after cell membrane opening by laser pulsing.

II. Porous Polymer Membrane Based Delivery Platform

In certain embodiments photothermal transfection platforms are fabricated using a porous membrane. Porous membranes are available in a wide variety of materials (e.g., nylon or nylon mesh, filter membranes, polytetrafluoroethylene (PTFE), expanded polytetrafluoroethylene (ePTFE), polyetheretherketone (PEEK), expanded polyetheretherketone (ePEEK), polyethylene (PE), polypropylene (PP), polyvinylidene fluoride (PVDF), ethyl vinyl acetate (EVA), thermoplastic polyurethane (TPU), polyethersulfone (PES), and the like). In various embodiments, porous rigid materials (e.g., porous ceramic) are also contemplated. Porous membranes are well known to those of skill in the art and are commercially available in a variety of pore sizes from a number of sources (see, e.g., Porex Corp. Fairburn Ga., and the like).

In certain embodiments a thin film (e.g., as described above) is deposited on the porous membrane. In certain embodiments the thin film is etched off the surface that is to be contacted with the cells, and optionally off the opposite surface as well. Thus, in certain embodiments, the surface contacted to the cells bears substantially no thin film.

Figure 6A:
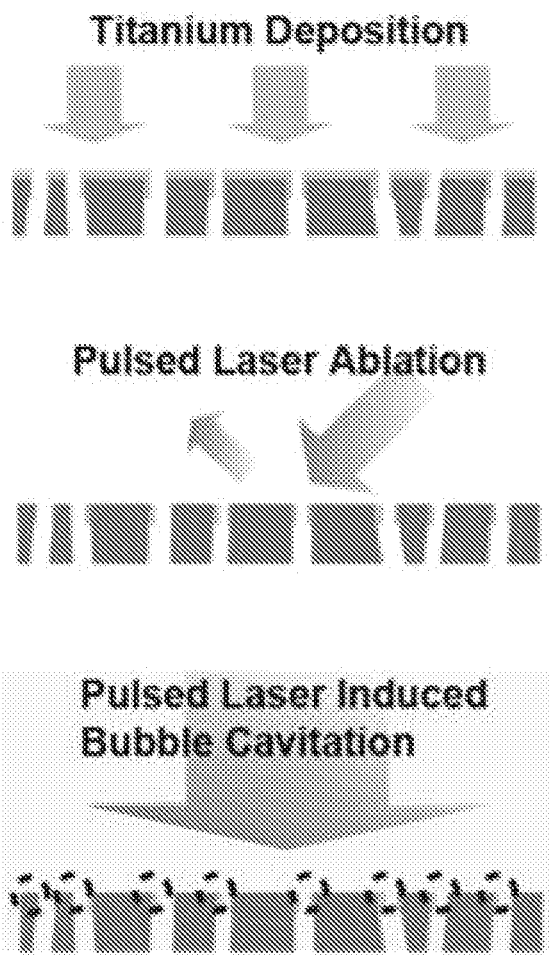
FIGS. 6A and 6B illustrate one embodiment of a porous polymer membrane based delivery platform.

FIG. 6A shows a parallel delivery platform realized in a porous polymer membrane. A titanium thin film was deposited onto track-etched polyester porous membranes. Using pulsed laser ablation at an oblique angle, the titanium thin film at the membrane surface was removed, leaving the titanium inside the pores intact. The sidewall titanium serves as bubble induction sites after pulsed laser excitation in order to create cutting in the adjacent cell membrane.

Figure 6B:
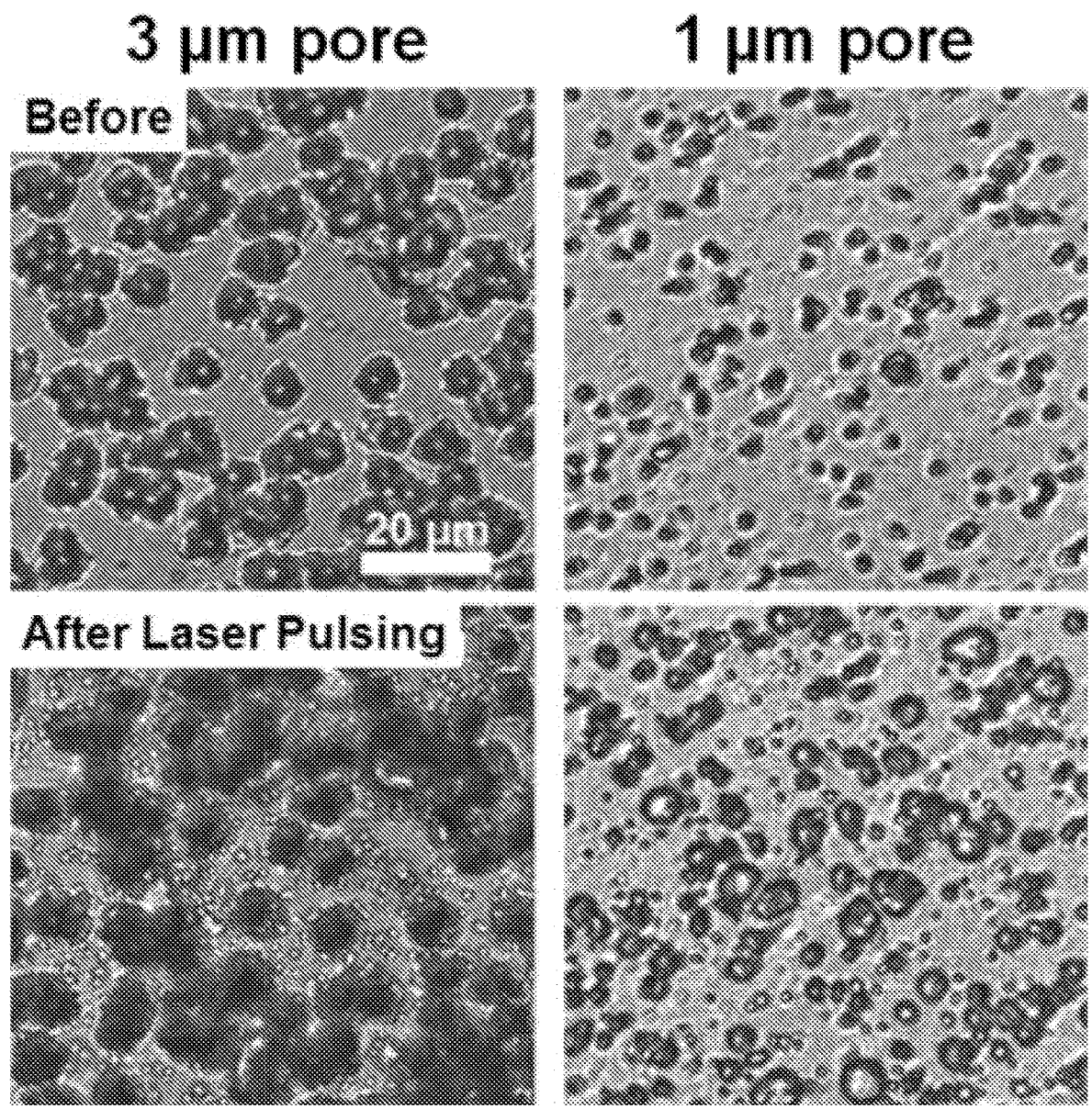
Figure 7:
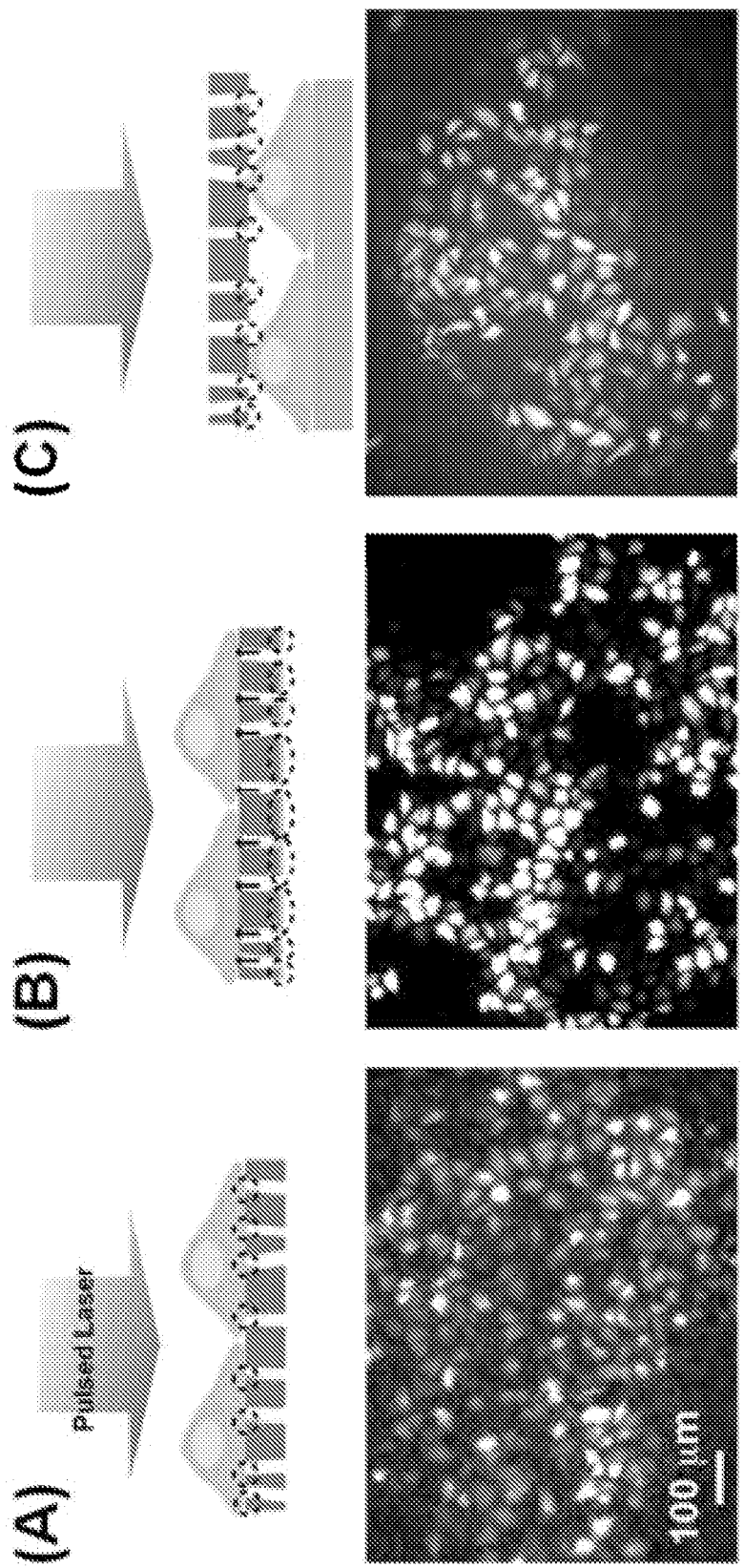
FIG. 7, panels A-C, illustrates different configurations of cargo delivery using the porous polymer membrane based photothermal platform. Fluorescent dextran delivery was demonstrated for all configurations. Panel A: Cells are grown on top of the porous membrane. Bubbles generated on the titanium thin film cuts the contacting cell membrane for delivery. Panel B: Cells are cultured on top of the porous membrane. Titanium thin film is deposited on the opposite (bottom) side of the porous membrane. Upon laser pulsing, bubble cavitation induces fluid flows through the pores and transiently permeabilizes the cell membrane. Panel C: Cells are grown on a separate substrate (e.g. coverslip, plastic petri dish). The titanium coated porous membrane was positioned on top of the cell for cell membrane poration and cargo delivery.
Figure 8:
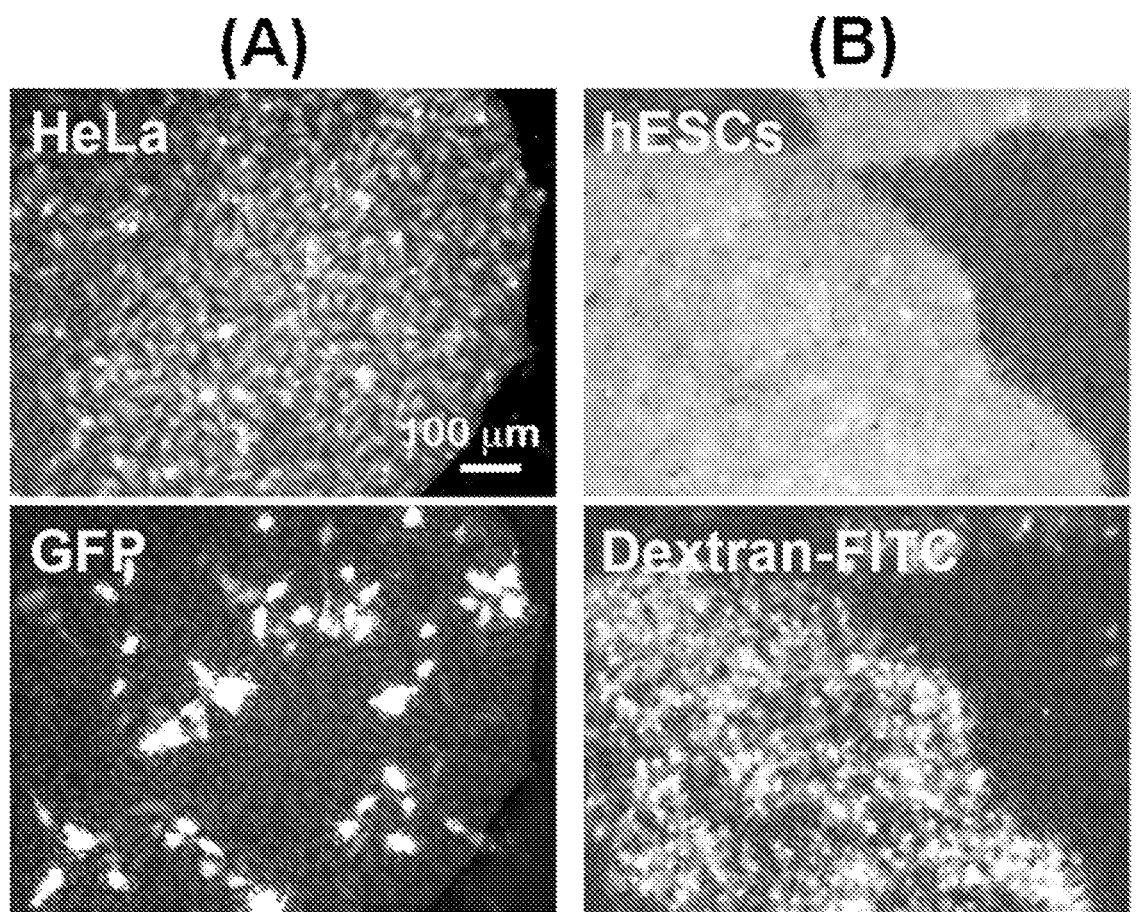
FIG. 8, panel A: Using the porous polymer membrane based photothermal platform, GFP encoding plasmid DNA was successfully delivered and expressed in HeLa cells.

FIG. 6B shows imaged cavitation bubbles generated on the porous membranes with average pore diameters of 3 μm and 1 μm respectively. Fabrication of this platform is simple and the polymer membrane can be made low cost and disposable after one time use. Cell membrane cutting and fluorescent dextran delivery was demonstrated in three different configurations as shown in FIG. 7, panels A-C. As illustrated in FIG. 7, panel A, cells can be deposited or grown on top of the porous membrane. Bubbles generated on the titanium thin film cuts the contacting cell membrane for delivery of the cargo (e.g., cargo provided in the medium surrounding the cells. As illustrated in FIG. 7, panel B, cells can be deposited or cultured on top of the porous membrane while the titanium thin film is present on (e.g. previously deposited on) the opposite (bottom) side of the porous membrane. Upon laser pulsing, bubble cavitation induces fluid flows through the pores and transiently permeabilizes the cell membrane. FIG. 7, panel C, illustrates an embodiment where cells are deposited on or are grown on a separate substrate (e.g. glass coverslip, plastic petri dish, culture vessel, microtiter plate, etc.). The titanium coated porous membrane was positioned on top of the cell for cell membrane poration and cargo delivery. Using the porous polymer membrane based photothermal platform, GFP encoding plasmid DNA was successfully delivered and expressed in HeLa cells. Fluorescent dextran molecules were delivered into human embryonic stem cell (hESC) colonies cultured on matrigel coated porous membranes with high efficiency as illustrated in FIG. 8.

It is noted that the porous membrane platform is well suited for delivery of large cargos such as plasmid DNA, RNA and proteins.

III. Bare Wafer Based Delivery Platform

Figure 9:
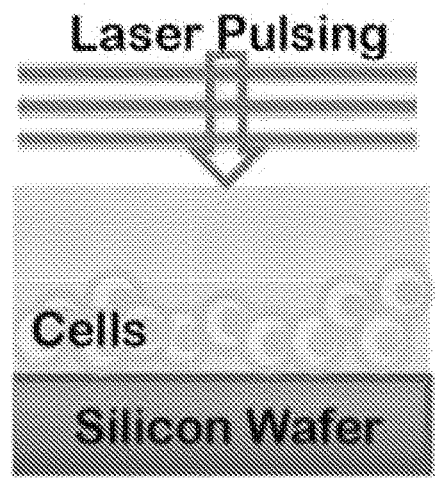
FIG. 9 illustrates one embodiment of a bare silicon wafer based delivery platform. The silicon wafer absorbs the pulsed laser light and the induced transient heating and cavitation on the silicon wafer surface permeabilizes cells cultured or positioned on top of the wafer. High-throughput, parallel delivery of small molecules such as calcein was demonstrated in non-adherent Ramos cells and adherent HeLa cells as shown.
Figure 9:
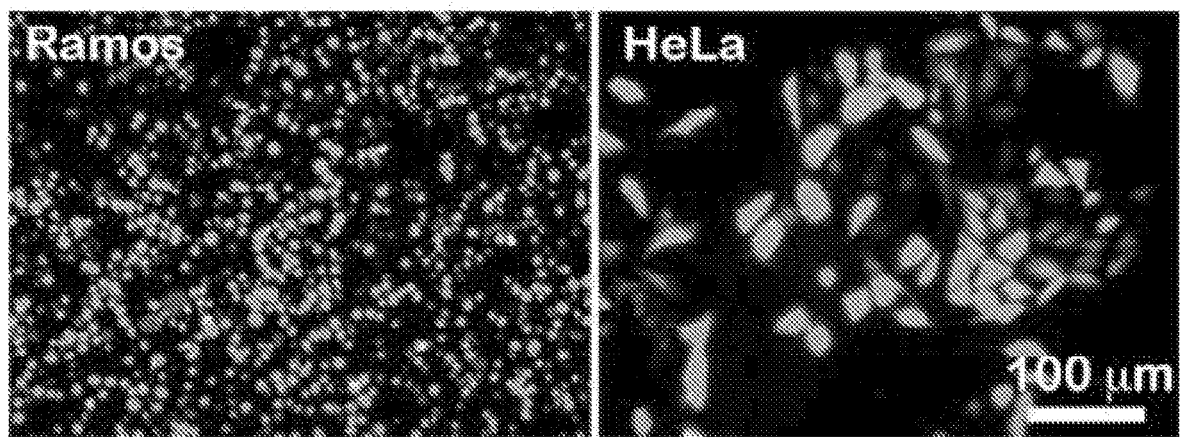

It was a surprising discovery that a substrate without a deposited film or nanoparticle (e.g. a bare wafer) can also be used as a photothermal delivery substrate. FIG. 9 illustrates a bare silicon wafer based platform. The silicon wafer absorbs the pulsed laser light and the induced transient heating and cavitation on the silicon wafer surface permeabilizes cells cultured or positioned on top of the wafer. High-throughput, parallel delivery of small molecules such as calcein was demonstrated in non-adherent Ramos cells and adherent HeLa cells.

For small molecules such as calcein and propidium iodide, the bare silicon wafer platform can be used. After laser pulsing and cargo delivery, cells can be harvested or continue to be culture on-chip for subsequent analyses.

The embodiments described herein are intended to be illustrative and non-limiting. Using the teaching provided herein, the configuration of such "photothermal delivery substrates" can be routinely varied changing for example, the features on the substrate (e.g., pore (orifice) size, size distribution, spatial distribution) can be changed, the type of film, the distribution and/or configuration of microfluidic channels, and the like.

Energy Sources and Selective Illumination.

Depending on the selection of materials, the substrates and/or thin film(s) comprising the photothermal delivery platforms surgical devices and/or substrates described herein can be excited (heated) by application of essentially any of a variety of methods. Such methods include, but are not limited to application of microwaves, lasers, non-coherent optical radiation (e.g., infrared radiation), electrical heating, electron spin resonance (ESR) heating, magnetic heating, and the like. In certain illustrative embodiments, heating thin film and/or substrate is accomplished by application of an optical energy source (e.g., a laser).

Where the or substrate is to be selectively heated (e.g., a portion of the substrate), it will be appreciated that any means of locally/selectively illuminating the device or substrate can be used. Thus, for example, in certain embodiments, local illumination of a particular region of the substrate can be accomplished by using, e.g., a focused laser or a focused non-coherent light (e.g., infrared) source.

In certain embodiments selective illumination of one or more regions of a substrate is accomplished by using a mask (shadow mask). In certain embodiments, local illumination can be achieved simply by focusing the illuminating energy source (e.g., laser) to a particular region using a lens and/or mirror system. In certain embodiments the energy source can be focused at a fixed region and the substrate moved (e.g., using a movable stage or other manipulator) to achieve local illumination of particular regions.

In certain embodiments the energy pulses (e.g., laser pulses) can be shaped by not only the static shadow masks as demonstrated in the examples, but also by dynamic masks using a spatial light modulator such as a TI's DMD microdisplay or LCD display. This provides real-time and interactive control of microinjection into target cells.

Particle/Nanoparticle/Thin Film Materials

In various embodiments the thin film(s) comprising the various devices described herein are fabricated from a metal, metal alloy, semiconductor, or other material that can be heated by the application of appropriate electromagnetic energy. In various embodiments semiconductors, metals, metal alloys, and oxides and/or nitrides thereof are contemplated. Depending on size, aspect ratio, film thickness, and/or material, such metals are readily heated using various energy sources (e.g., laser light, electric field, RF field, magnetic field, ultrasonic source, etc.).

While most of the discussion provided herein pertains to semiconductor or metal films, and the examples describe titanium films, the materials heated by the energy source need not be so limited. Essentially any material that absorbs the appropriate energy with resultant heating can be used for the heating material in the methods and devices described herein. Accordingly, in certain embodiments, films comprising materials such as gold, silver, tantalum, platinum, palladium, rhodium, or titanium, or oxides, nitrides, or alloys thereof are contemplated.

One important material useful in the thin film(s) comprising devices and systems described herein is titanium (Ti) and/or oxides, nitrides, alloys or doped oxides, doped nitrides, or alloys thereof. In certain embodiments the thin film(s) comprising systems and methods described herein comprise titanium and/or titanium nitride (TiN), which is a very hard material with a melting temperature three times higher than gold.

Other variants of TiN are well known to those of skill in the art. These include, but are not limited to titanium carbon nitride (TiCN) and titanium aluminum nitride (TiAlN), which can be used individually or in alternating layers with TiN or in mixed particle populations with TiN particles. These coatings offer similar or superior enhancements in corrosion resistance and hardness, and different (even tunable) absorption properties.

As indicated above, the films comprising the devices and/or substrates described herein need not be limited to materials comprising metals.

In various embodiments thin films comprising one or more materials from Groups II, III, IV, V, or VI of the periodic table are also contemplated as well as oxides, nitrides, alloys, and doped forms thereof and/or transition metals, transition metal oxides, transition metal nitrides, alloys or composites comprising transition metals, and the like are contemplated. In certain preferred embodiments, the nanoparticles and/or films comprise Group II, Group III, Group IV, Group V materials (e.g., carbon, silicon, germanium, tin, lead), doped Group II, III, IV, V, and VI elements, or oxides of pure or doped Group II, III, IV, V, or VI elements or transition metals, transition metal oxides or transition metal nitrides. In certain preferred embodiments the particles/nanoparticles and/or thin films comprise a Group III, IV, or V semiconductor.

It will be understood from the teachings herein that in certain embodiments, the thin films include one or more materials such as Si, Ge, SiC, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, and their oxides and nitrides.

As indicated above, in various embodiments, the group II, III, IV, V, or VI element, transition metal, transition metal oxide or nitride comprising thin film can be essentially pure, or it can be doped (e.g., p- or n-doped) and/or alloyed. P- and n-dopants for use with Group II-VI elements, in particular for use with Groups III, IV, and V elements, more particularly for use with Group IV elements (e.g., silicon, germanium, etc.) are well known to those of skill in the art. Such dopants include, but are not limited to phosphorous compounds, boron compounds, arsenic compounds, aluminum compounds, and the like.

In certain embodiments the films comprise Group IV semiconductors such as silicon, germanium, and silicon carbide. The most common dopants for such semiconductors include acceptors from Group III, or donors from Group V elements. Such dopants include, but are not necessarily limited to boron, arsenic, phosphorus, and occasionally gallium.

As indicated above, in various embodiments, thin films comprise a semiconductor. Many doped Group II, III, IV, V, or VI elements are semiconductors and include, but are not limited to, ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, $Cd_3Sb_2$, $Zn_3P_2$, $Zn_3As_2$, $Zn_3Sb_2$, $TiO_2$, $TiO_2$, $TiO_2$, $Cu_2O$, CuO, $UO_2$, $UO_3$, $Bi_2O_3$, $SnO_2$, $BaTiO_3$, $SrTiO_3$, $LiNbO_3$, $La_2CuO_4$, $PbI_2$, $MoS_2$, GaSe, SnS, $Bi_2S_3$, GaMnAs, InMnAs, CdMnTe, PbMnTe, $La_{0.7}Ca_{0.3}MnO_3$, FeO, NiO, EuO, EuS, $CrBr_3$, $Cu(In,Ga)Se_2$, $Cu_2ZnSnS_4$, $CuInSe_2$, $AgGaS_2$, $ZnSiP_2$, $As_2S_3$, PtSi, $BiI_3$, $HgI_2$, TlBr, Se, $Ag_2S$, $FeS_2$, Ge and Si and ternary and quaternary mixtures thereof, and the like.

In addition to laser energy, in certain embodiments, magnetic, electric fields, and RF fields can also readily be used to heat certain thin films. Thus, for example, U.S. Patent Publication No: 2007/0164250, which is incorporated herein by reference, provides magnetic materials that when placed in a magnetic field are selectively heated at a certain frequency of the magnetic field.

In various embodiments such films comprise magnetic materials (such as the Ferro V magnetic pigment) that transduce energy when exposed to a magnetic field of sufficient intensity. Thus, for example, an alternating magnetic field will induce an alternating current in the particle, producing heat. A variety of magnetic materials can be used. Such materials include, but are not limited to magnetic materials, such as $Fe—O_4$, $Fe_2O_3$. Also, in certain embodiments, silver, copper, platinum, palladium and the like can comprise the particles, nanoparticles, and/or thin films used in the devices of this invention. In certain embodiments the particles, nanoparticles, and/or thin films can comprise $TiO_2$, $CeO_2$, Ag, CuO, yttrium aluminum garnet (YAG), $InO_2$, CdS, $ZrO_2$, or a combination thereof. In another embodiment, any metal oxide, metal alloy, metal carbide, and/or transition metal, may be used in the instant invention. In some embodiments, the particles can be coated, such that the coating does not alter their respective responsiveness to the applied field.

In certain embodiments thin films used in the devices of the present invention can be made of magnetic materials, while in other embodiments, they can be made of or comprise paramagnetic or superparamagnetic materials.

Accordingly, in certain embodiments thin films can comprise a paramagnetic or superparamagnetic material that can be heated using electron spin resonance absorption (SPM) and/or ferromagnetic resonance. Electron spin resonance (ESR) heating and ferromagnetic resonance (FMR) heating are described in US Patent Publications 2006/0269612 and 2005/0118102, which are incorporated herein by reference. Yttrium-iron garnet $Y_3Fe_5O_{12}$ and $\gamma$-$Fe_2O_3$ are two well-known materials suitable ESR and/or FMR heating. Different dopants can be added to lower the spin resonance frequencies of these materials various applications. Magnetic garnets and spinels are also chemically inert and indestructible under normal environmental conditions.

Also contemplated are various materials and/or semiconductors comprising materials from Groups II, III, IV, and V of the periodic table.

In certain embodiments, the area and/or thickness of the thin film(s) for use in the devices described herein can be adjusted or optimized and reflect the choice of the film material, the nature of the excitation energy, and frequency and/or strength of the excitation energy.

In various embodiments, where present, thin films range in thickness from about 0.5, 1, 2, 5, 10, 50, 100, 150, 200, 300, 400, or 500 nm to about 800 nm, 1 μm, 5 μm, 10 μm, 50 μm, or 100 μm. In certain embodiments the metal films range in thickness from about 2 nm or 5 nm, 10 nm, 20 nm, or 30 nm to about 100 nm, 300 nm, 500 nm, 800 nm or 1 μm. In certain embodiments the metal films range in thickness from 1 nm to 150 nm, preferably from about 5 nm to 100 nm, more preferably from about 5 nm, 10 nm, or 20 nm to about 50 nm, 75 nm, or 100 nm. In certain embodiments the metal films are about 30 nm in thickness.

In various embodiments the coated layer comprising the devices described herein can be a continuous thin film, or a thin film broken up into multiple domains (e.g., 5 nm, 10 nm, 20 nm, 50 nm, 100 nm, 200 nm, 500 nm domains). The shape of domains and the thickness of thin films will affect the absorption spectrum of the material and the energy source and intensity required to produce the desired local heating.

In general, the film thickness affects the size of the bubble(s) produced by local heating and the nature of the microfluidic flow near the bubbles. This determines the shear stress produced and the size of the opening(s) produced in the cell. In general, the thicker the film, the larger the bubble produced and the larger the hole(s) produced in the cell(s).

Application of Films to Substrates.

Methods depositing thin films on surfaces are well known to those of skill in the art.

For example, thin films can be deposited by any suitable method including but not limited to sputtering deposition, chemical vapor deposition (CVD), molecular beam epitaxy (MBE), plasma-assisted vapor deposition, cathodic arc deposition or Arc-PVD, and electron beam evaporation deposition. In certain embodiments thin films can also be chemically deposited on the photothermal transfection substrate.

The most common methods of TiN thin film creation are physical vapor deposition (PVD, usually sputter deposition, Cathodic Arc Deposition or electron beam heating) and chemical vapor deposition (CVD). In both methods, pure titanium is sublimated and reacted with nitrogen in a high-energy, vacuum environment.

Bulk ceramic objects can be fabricated by packing powdered metallic titanium into the desired shape, compressing it to the proper density, then igniting it in an atmosphere of pure nitrogen. The heat released by the chemical reaction between the metal and gas is sufficient to sinter the nitride reaction product into a hard, finished item.

The methods of forming thin films on a surface described above are illustrative and not intended to be limiting. Using the teachings provided herein, other thin film coated surfaces can be produced using at most routine experimentation.

Cell Types

It is believed the methods and devices described herein can be used with essentially any cell having a cell membrane. In addition, the methods and devices can also be used on cells having a cell wall. Accordingly, in various embodiments, animal cells (e.g., mammalian cells) and plant cells and fungal cells are contemplated.

Thus, for example, adherent cells including NIH3T3 mouse fibroblasts, HEK293T embryonic kidney fibroblasts, and HeLa cervical carcinoma cells have been injected GFP-expressing plasmids using the devices and methods described herein. In general, it is believed that any adherent mammalian cell type can be easily injected using the devices and methods described herein because: 1) the laser fluence that is determined as optimal in terms of effective hole-punching and maintaining cell viability is lies with in a relatively narrow range for all the cell types tested; and 2) adherent cell features used to determine appropriate injection location (e.g., perinuclear or possibly nuclear) are easily identified visually.

Lymphocytes, stem cells of various types, germ cells and others are non-adherent, but it is often desirable to inject or perform other "surgical" procedures on such cells. Integration of optical tweezers with the cell surgery tool as described herein, makes this possible.

In addition, using the methods and devices described herein, injecting individual cells within a cell cluster, such as is required to grow human embryonic stem cells and maintain pluripotency, is achievable especially on the surface of stem cell clusters using the methods and devices described herein. It is also believed to be possible to stereotactically inject specific cells within clusters, which is desirable for a variety of reasons (e.g., developmental tracking, establishing gradients, etc.).

Deliverable Materials.

It is believed possible to deliver essentially any desired material into a cell using the methods and devices described herein. Such materials include, but are not limited to nucleic acids, proteins, organelles, drug delivery nanoparticles, probes, labels, and the like. Delivery of plasmid DNAs into cells using the methods described herein as been demonstrated already in at least three adherent cell types. Accordingly any plasmid-sized genetic material should be easily transferred by the methods and devices described herein.

BACs (bacterial artificial chromosomes)—a desired goal for hard to transduce cells and for delivery vehicles with size restrictions (plasmids, retroviruses, lentiviruses) for introducing large genetic anomalies or for tracking the regulated expression of specific genes during development.

Accordingly, it is believed the devices and methods described herein can be used to deliver whole or partial natural or synthetic chromosomes. Similar to BACs, large chromosomes or chromosomal fragments that cannot be transduced into most cell types by previous methods could be transferred into cells by our methods, for example, to establish models of human trisomy disorders (e.g., Down and Klinefelter syndromes).

Similarly the methods can be used for the transfer of nuclei (e.g., in somatic nuclear transfer), or other organelles (e.g., mitochondria, or nanoengineered structures) can readily be introduced into cells.

In various embodiments the deliverable materials comprise a reagent includes, but is not limited to a reagent selected from the group consisting of nucleic acids (including, for example, vectors and/or expression cassettes, inhibitory RNAs (e.g., siRHA, shRNA, miRNA, etc.), ribozymes, proteins/peptides, enzymes, antibodies, imaging reagents, organelles (e.g., nuclei, mitochondria, nucleolus, lysosome, ribosome, etc.), chromosomes, intracellular pathogens, inanimate particles, such as quantum dots, surface-enhanced, Raman scattering (SERS) particles, microbeads, and the like.

Modular Systems.

In certain embodiments the transfection platforms described herein are provided as a "module" that can readily be integrated with existing equipment. For example, in certain embodiments, the transfection substrate is provided in a format that can be added to or that can replace a stage on an existing microscope. In certain embodiments the substrate is formatted to replace and x/y/z stage on an inverted microscope (e.g., a Zeis inverted microscope).

In certain embodiments the transfection substrates are provided as a microfluidic system (e.g., a lab on a chip system) and/or as a module that can be integrated with microfluidic systems.

Patterned Transfection Systems.

In various embodiments this invention contemplates systems efficient high throughput delivery of a reagent (cargo) into cells (cell transfection). In certain embodiments systems comprising one or more photothermal substrates comprise a cell transfection substrate (e.g., photothermal substrate) as described herein. The substrate typically bears cells and/or a cell culture. The system can optionally comprise means for delivering reagents, agents to be transfected into the cell(s), means for masking portions of the substrate from an electromagnetic energy source (e.g., optical energy source), and the like.

In certain embodiments the systems optionally further include a source of electromagnetic energy to heat the thin film and/or photothermal substrate. Suitable sources include, but are not limited to a laser, a high-intensity non-coherent light source, a magnetic field generator, an RF field generator, and the like.

In various embodiments the systems can include a controller (e.g., a laser controller). In certain embodiments the controller can be configured to control the intensity and/or duration and/or wavelength of an illumination source and/or the pattern of illumination of the photothermal substrate. In certain embodiments the controller detects and/or controls flow of reagents through microchannels comprising the photothermal substrate and/or a microfluidic system within which the photothermal substrate is disposed. Where the photothermal substrate is provided on a microscope (e.g., an inverted microscope) the controller can, optionally control the microscope stage, the microscope focus, and/or image acquisition from the microscope.

Kits.

In another embodiment, kits are provided for efficient height-throughput delivery of cargo into cells. In certain embodiments the kits comprise a container containing a photothermal delivery device as described herein. In various embodiments the kits can optionally additionally include any of the reagents or devices described herein (e.g., reagents, buffers, tubing, indicators, manipulators, etc.) to perform cargo delivery into cells.

In addition, the kits optionally include labeling and/or instructional materials providing directions (i.e., protocols) for the use the systems and devices described herein to deliver a cargo into a cell.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for delivering an agent into a plurality of cells, the device comprising:
   a track etched porous membrane comprising a plurality of pores, wherein a thin film coating of a metal or a metal alloy is disposed within the plurality of pores of said porous membrane and the surface of said porous membrane is substantially free of said coating, and wherein said porous membrane is disposed in a vessel configured to contain, during use, a cell medium and said plurality of cells disposed within said cell medium; and
   a pulse laser that produces optical radiation focused on the top surface of said porous membrane, wherein said laser is capable of heating said thin film coating to generate cavitation bubbles within said cell medium wherein said cavitation bubbles are capable of transiently opening cell membranes of said plurality of cells for delivery of said agent into said plurality of cells: and
wherein said vessel contains said plurality of cells and said cell medium and said porous membrane is disposed on top of said plurality of cells.

2. The device of claim 1, wherein the average pore size of pores in said porous membrane ranges from about 100 nm up to about 3 μm before deposition of said thin film.

3. The device of claim 1, wherein said metal or said metal alloy comprises a material selected from the group consisting of gold, silver, titanium (Ti), TiN, TiCn, and TiAlN.

4. The device of claim 1, wherein said thin film ranges in thickness from about 10 nm up to about 1 μm.

5. The device of claim 1, wherein said porous membrane is a porous alumina (Al2O3) structure or a porous polyester membrane.

6. The device of claim 1, wherein the device comprises a controller that adjusts at least one of the pattern of illumination by the pulse laser, the timing of occurrence of light pulses emitted by the pulse laser, the frequency of occurrence of pulses emitted by the pulse laser, the wavelength of pulses emitted by the pulse laser, the energy of pulses emitted by the pulse laser, and the aiming or the location of pulses emitted by the pulse laser.

7. A method of delivering the agent into one or more cells, said method comprising:
   i) providing the device according to claim 1;
   ii) contacting the plurality of cells with the agent by introducing the agent into the cell medium; and
   iii) exposing a region of the porous membrane disposed on the plurality of cells to the optical radiation produced by said laser thereby inducing the heating of the thin film in the pores of said porous membrane in the irradiated region where the heating forms the cavitation bubbles in the cell medium that introduce the openings in the membrane of one or more of the plurality of cells that are in or near the heated region resulting in the delivery of the agent into the one or more of the plurality of cells.

8. The method of claim 7, wherein said method comprises placing or growing the plurality of cells on a separate substrate and the porous membrane is positioned on top of the separate substrate comprising the plurality of cells.

9. The method of claim 8, wherein said separate substrate comprises a surface of an object selected from the group consisting of a coverslip, a microtiter plate, a petri dish, and a culture vessel.

10. The method of claim 7, wherein the agent is selected from the group consisting of a nucleic acid, a chromosome, a protein, a label, an organelle, and a small organic molecule.

11. A device for delivering an agent into a plurality of cells, the device comprising:
    a track etched porous membrane comprising a plurality of pores, wherein a thin film coating of a metal or a metal alloy is disposed within the plurality of pores of said porous membrane and the surface of said porous membrane is substantially free of said coating, and wherein said porous membrane is disposed in a vessel configured to contain, during use, a cell medium and said plurality of cells disposed within said cell medium, and said porous membrane is positioned to support or to rest on the plurality of cells when the plurality of cells and the cell medium are present in said vessel:
    a pulse laser that produces optical radiation focused on the top surface of said porous membrane, wherein said laser is capable of heating said thin film coating to generate cavitation bubbles within said cell medium wherein said cavitation bubbles are capable of transiently opening cell membranes of said plurality of cells for delivery of said agent into said plurality of cells: and wherein said device comprises at least one of a lens system, a mirror system, a mask, and a positioning system to direct the optical radiation from an optical radiation source in said pulse laser to a specific region of said porous membrane.

12. The device of claim 1, wherein said device comprises a half-wave plate.

13. The device of claim 1, wherein said device comprises a polarizer.

14. The device of claim 13, wherein said polarizer comprises a polarizing beam splitter cube.

15. A device for delivering an agent into a plurality of cells, the device comprising:

a track etched porous membrane comprising a plurality of pores, wherein a thin film coating of a metal or a metal alloy is disposed within the plurality of pores of said porous membrane and the surface of said porous membrane is substantially free of said coating, and wherein said porous membrane is disposed in a vessel configured to contain, during use, a cell medium and said plurality of cells disposed within said cell medium, and said porous membrane is positioned to support or to rest on the plurality of cells when the plurality of cells and the cell medium are present in said vessel:

a pulse laser that produces optical radiation focused on the top surface of said porous membrane, wherein said laser is capable of heating said thin film coating to generate cavitation bubbles within said cell medium wherein said cavitation bubbles are capable of transiently opening cell membranes of said plurality of cells for delivery of said agent into said plurality of cells: and wherein said device comprises an objective lens configured to focus the optical radiation from said optical radiation source onto said porous membrane.

* * * * *